(12) United States Patent
Bäbler et al.

(10) Patent No.: US 6,951,075 B2
(45) Date of Patent: *Oct. 4, 2005

(54) PIGMENT CONCENTRATES FOR COLORING SEEDS

(75) Inventors: Fridolin Bäbler, Hockessin, DE (US); Kenneth Schumann, Atlanta, GA (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 135 days.

This patent is subject to a terminal disclaimer.

(21) Appl. No.: 10/400,419

(22) Filed: Mar. 27, 2003

(65) Prior Publication Data

US 2003/0221365 A1 Dec. 4, 2003

Related U.S. Application Data

(60) Provisional application No. 60/373,504, filed on Apr. 18, 2002.

(51) Int. Cl.$^7$ ............................. A01C 1/06; A01C 21/00
(52) U.S. Cl. ...................... 47/57.6; 47/DIG. 9; 504/100
(58) Field of Search ........................... 47/57.6, DIG. 9; 504/100

(56) References Cited

U.S. PATENT DOCUMENTS

| | | | |
|---|---|---|---|
| 3,550,868 A | 12/1970 | Stephanoff | 241/5 |
| 3,595,486 A | 7/1971 | Stephanoff | 241/5 |
| 3,648,936 A | 3/1972 | Stephanoff | 241/5 |
| 3,856,215 A | 12/1974 | Van Vliet | 241/39 |
| 4,272,417 A | 6/1981 | Barke et al. | 260/22 |
| 4,368,591 A | 1/1983 | Barke et al. | 47/57.6 |
| 4,448,796 A * | 5/1984 | Wieser et al. | 427/4 |
| 4,853,429 A | 8/1989 | Sannan et al. | 524/29 |
| 4,881,343 A | 11/1989 | Sannan et al. | 47/57.6 |
| 5,087,475 A | 2/1992 | Bazin et al. | 427/4 |
| 5,137,747 A | 8/1992 | Malandain et al. | 427/4 |
| 5,470,581 A | 11/1995 | Grillo et al. | 424/479 |
| 5,527,760 A * | 6/1996 | Rensing et al. | 504/100 |
| 5,584,922 A | 12/1996 | Bäbler | 106/417 |
| 5,667,580 A | 9/1997 | Bäbler | 106/499 |
| 5,746,022 A | 5/1998 | Brown et al. | 47/57.6 |
| 5,843,220 A | 12/1998 | Bäbler | 106/415 |
| 5,849,320 A | 12/1998 | Turnblad et al. | 424/410 |
| 5,931,997 A | 8/1999 | Bäbler | 106/410 |
| 6,063,182 A | 5/2000 | Bäbler | 106/506 |
| 6,688,041 B2 * | 2/2004 | Babler et al. | 47/57.6 |

FOREIGN PATENT DOCUMENTS

WO 99/66784 12/1999

OTHER PUBLICATIONS

Southern Agricultural Insecticides, Inc., 20–20–20 Soluable Fertilizers with Minor Elements, revised 1998.*

* cited by examiner

Primary Examiner—Michael J. Carone
Assistant Examiner—Susan C. Alimenti
(74) Attorney, Agent, or Firm—Tyler A. Stevenson; Kevin T. Mansfield

(57) ABSTRACT

The present invention relates to the use of a pigment form or pigment concentrate comprising of an organic pigment, a growth-promoting additive, and optionally inorganic filler and/or an organic additive for coloring of seeds. Seeds colored by the dry pigment forms or pigment concentrates show homogeneous color and in some cases growth promotion effects.

27 Claims, No Drawings

PIGMENT CONCENTRATES FOR COLORING SEEDS

This application claims benefit of U.S. Provisional Application No. 60/373,504 filed Apr. 18, 2002.

FIELD OF THE INVENTION

The present invention relates to instant pigment forms and pigment concentrates, in particular pigment concentrates comprising of an organic pigment, and/or optionally inorganic filler and a growth-promoting additive, a method for its preparation and the use of the pigment concentrate for coloring seeds, and enhancing growth.

BACKGROUND OF THE INVENTION

Seeds are often treated to reduce yield losses during cultivation and for enhancing the agronomic and nutritional value of the produce. Such treating agents are for example fungicides, insecticides, rodenticides, nematocides, miticides or bird repellents. Furthermore, many varieties of genetically altered crops are coming to the market. Treated and/or genetically modified seeds must be marked in order to distinguish them from the untreated and unmodified seeds. The marking of seeds is particularly beneficial for farmers who then can easily distinguish the chemically treated and modified seeds for plantings from e.g. cereal grains for consumption.

A number of patents describe processes for the marking and coating of seeds by active ingredients and film forming compositions. U.S. Pat. No. 5,087,475 discloses a process for the film coating of materials using a water- and gas-permeable, adhesive film-forming substance, which consists of spraying the film-forming substance on seed materials and drying the seed materials. The spraying and drying steps are carried out simultaneously using a compact volume of seed materials in motion. The film-forming substance is supplied in the form of a solution or a suspension. U.S. Pat. No. 5,470,581 discloses a process for providing an aqueous film coating from a combination of maltodextrin and cellulosic polymers for pharmaceutical tablets, candy, cereals and agricultural seeds. The aqueous suspension can be applied by spraying. The aqueous suspension can contain a colorant. U.S. Pat. No. 5,849,320 discloses a process for coating a seed with an insecticide.

U.S. Pat. Nos. 4,853,429 and 4,881,343 describe an aqueous medium containing a dye or pigment and a binder resin composed of the salt of chitosan and an organic acid for seed coloring. The patents indicate that the colorant is used at a concentration of about 0.1 to 10% by weight based on the aqueous medium and exemplifies using C.I. Pigment Green 7, C.I. Pigment Green 128 and C.I. Pigment Red 122 at 2.5% concentration. The patents do not indicate the form or solids content of said pigments.

U.S. Pat. No. 5,746,022 discloses a seed color coating using a poly oxyalkylene substituted chromophore in the coating. The coating composition contains a solvent, binder, colorant and other optional additives. The coating composition is applied as a film coating by spraying a solution, dispersion and/or suspension onto the seeds. The aqueous-based coating composition is described as containing 5 to 80 parts biologically active agents, 20 to 45 parts water, 1 to 15 parts binder and 0.1 to 50 parts colorant. In Example 11, the coloring composition consists of 310 parts lime, 170 parts water, 30 parts poly (vinyl alcohol) binder and 1 part of green colorant (37% solids).

U.S. Pat. No. 4,272,417 discloses a liquid seed coating composition containing a binding agent, an active ingredient and a coloring agent in a liquid medium including water and a polyol. The suggested colorants are selected from dyes, pigments and lakes. The coloring agent is selected for solubility and/or dispersibility in the liquid system. The patent does not disclose any means for producing a so-called dispersible pigment. The coloring agent is present at between 0.1 to 3 percent by weight, preferably 0.4 percent by weight of the total composition. The solids content of the colorant is not provided.

U.S. Pat. No. 4,368,591 discloses seeds that are coated with an active ingredient and between 0.035 and 1.8 grams of titanium dioxide per kilogram of seed in either rutile or anatase form. The titanium dioxide allegedly provides a bright, opaque coating on the seeds. The active ingredient and particulate titanium dioxide are applied onto the seeds in an aqueous medium. The particulate titanium dioxide is in dispersion in the aqueous medium. The dispersion contains between 10 and about 100 grams of insoluble titanium dioxide per liter of dispersion.

U.S. Pat. No. 5,137,747 claims a process for drying a germinative substrate of grains or seeds which have been wetted in a coating or surface film forming treatment by dusting the substrate with a desiccant powder consisting of at least one alumina silicate and which is substantially free of components which would interfere with germination of the substrate. Although these desiccant powders can contain pigments due to the high alumina silicate content they tend to be low in coloring strength.

Published PCT application WO 99/66784 discloses a process for coating seeds with a thin coating of a pigment that selectively allows light rays having wavelengths of about 570 to 700 nm to pass there through, or, in the alternative, selectively reflects light rays having wavelengths of about 420 to about 520 nm. The applicants exemplified seeds that were coated with a red pigment, which reflected approximately from 600 to 700 nm, a blue pigment, which reflected approximately 400 to 500 nm, and a green pigment, which reflected approximately 500 to 570 nm. The green pigment produced the greatest budding ratio with respect to the selected seed. The application does not provide any showing of a control set of seeds in order to assess improvement without any pigment coating.

Even though the known processes can deliver marked seeds, they are often environmentally unfriendly since they use aqueous dyes which can cause colored effluents. Most commercially available organic pigment particles are not wettable in aqueous mediums and require the addition of surfactants or hydrophilic copolymers. However, current seed coloring systems have also employed coating compositions that contain aqueous pigment dispersions, which have a low solid pigment concentration. Despite the presence of surfactants, the aqueous dispersions of pigment can settle out as function of time. Additionally, such surfactants can have a negative impact on the growth of the seeds or can negatively interact with other active coating ingredients generating an undesirable gel. Furthermore, aqueous pigment dispersions, delivered in drums need a large, and in winter, heated storing area to avoid freezing.

SUMMARY OF THE INVENTION

Applicants discovered, that the above mentioned disadvantages can be avoided using pigment compositions comprising organic pigments that have been treated in a particular manner to produce a highly dispersible pigment concentrate. Examples of such pigment compositions are described in patents such as for example U.S. Pat. No.

5,584,922 No. 5,667,580. Particularly preferred examples are described in U.S. Pat. No. 5,931,997, U.S. Pat. No. 5,843,220 and U.S. Pat. No. 6,063,182. Each of these patents are incorporated herein by reference. These patents disclose pigments that are readily dispersible to color high molecular weight substrates like for example plastics, automotive paints or inks. The patents do not suggest that the stir-in pigments described therein would be suitable for coloring seed materials or disclose aqueous dispersions. Surprisingly, by blending such pigments with appropriate known growth enhancement additives and applying them on seeds synergistically stronger growth enhance effects can be observed.

DETAILED DESCRIPTION OF THE INVENTION

The present invention describes pigment forms and pigment concentrates which can be effectively, and due to their high color strength, economically be used for seed coloring. Such pigment forms and pigment concentrates do not have any adverse effect to seeds, but color the seeds and additionally can manifest germination-promoting effects.

The present invention is drawn to a colored seed having an exterior surface that is coated substantially in its entirety with an organic pigment that is characterized by a masstone reflection spectrum from 400 nm to 700 nm having a first peak from 400 nm to 520 nm with a maximum at 460 nm+/−10 nm, a second peak from 540 to 680 nm having a maximum at 630 nm+/−10 nm and a positive slope from 680 to 700 nm. A particularly preferred pigment capable of enhancing seed germination is copper phthalocyanine described in U.S. Pat. No. 5,931,997.

In order to measure the reflection spectrum, the inventive pigment is first incorporated into a substrate, such as for example a basecoat/clearcoat paint system like those described in Examples 2A and 2D of U.S. Pat. No. 5,931,997. It is the reflection spectrum of the pigmented substrate, such as the coated panel or a pigmented plastic sheet, which is measured. The reflection spectra are measured at "complete hide" which means that the substrate is pigmented such that any background color is not observable. For example, at "complete hide" it is not possible to see the background color of a coated panel or a background color through a pigmented plastic sheet. A masstone reflectance spectrum is the reflectance spectrum observed when the inventive pigment is the only pigment used to color the substrate.

When incorporated into a basecoat/clearcoat paint system to complete hide, the inventive copper phthalocyanine pigment yields a masstone coated panel that is characterized by a reflection spectrum having a maxima above 6 percent at 460 nm+/−10 nm and a reflection at 480 nm above 5 percent, a reflection at 620 nm above 4.6 percent and a reflection at 700 nm above 4.5 percent. In particular, the masstone reflection spectrum shows a reflection at 480 nm above 5.3 percent, in particular from 5.3 to 5.4 percent, a reflection at 620 nm above 4.7 percent, in particular from 4.7 to 4.9 percent, and a reflection at 700 nm above 4.7 percent, in particular from 4.7 to 4.8 percent.

In general, at least 95 percent of the particles in the pigment concentrate have a particle size in the range from 0.1 µm to 9 µm with at least 50 percent of the particles having a particle size in the range from 0.5 µm to 3.5 µm. Based on these average particle size ranges, it is clear that such pigments are used in the form of a pigment crude or a conditioned pigment. Preferably, at least 50 percent of the particles have a particle size in the range from 0.8 to 2.5 µm. The largest dimension (e.g. length) of the pigment particle is measured to determine the particle size.

Particle size is determined by an electron micrograph or by laser diffraction using a Fraunhofer diffraction instrument. However, electron microscopy is a more reliable method for determining the presence of small particles, for example those with a particle size below 0.1 µm.

The copper phthalocyanine pigment is not platelet-shaped. In particular, the preferred pigment concentrate is composed mostly of pigment particles having a prismatic shape wherein the particles have a length, which is more than three times the width and the particle thickness is at least one third the width.

The preferred pigment form is prepared by direct synthesis or by an appropriate conditioning method, such as, for example, recrystallization of a premilled copper phthalocyanine in an appropriate organic solvent or mechanically breaking commercially available copper phthalocyanine crude, which generally has needle-prismatic shape and a particle size distribution wherein about 50 percent or more of the particles have a particle size in the range from 1.5 to 5 µm, but wherein a significant number of particles, for example, greater than 5 percent, are larger than 9 µm, for example, up to 45 µm.

Although the preferred copper phthalocyanine pigment shows excellent dispersibility and a remarkably good flocculation resistance for a beta copper phthalocyanine pigment, in order to further improve the pigment properties of the inventive copper phthalocyanine pigment, texture-improving agents and/or anti-flocculants are can be added before, during or after the corresponding preparatory process.

The preferred pigment form is prepared by subjecting an organic pigment, which organic pigment is a pigment crude or a recrystallized, large-particle-size organic pigment, preferably a copper phthalocyanine, to an air jet milling step. Air jet milling is known and described for example in DE 2042626, U.S. Pat. No. 3,856,215, U.S. Pat. Nos. 3,648,936, 3,595,486 and 3,550,868, which are here incorporated by reference. Air jet mills such as the JET-O-MIZER™ or MICRO-JET™ are commercially available from Fluid Energy Processing and Equipment Company, Plumsteadville, Pa. 18949.

In general, air jet milling selectively reduces the particle size mainly of those particles in the sample, which are outside of the desired particle size range. Thus, the average particle size of the air-jet-milled sample usually changes only slightly after the milling step, but the particle size distribution of the particles in the sample is within a much narrower range.

In comparison to other conditioning methods, for example wet milling, the air jet milling process provides pigment particles with fewer small splinter particles. The pigmentary crystal fragments maintain a clean, practically unbroken surface, as is seen by electron microscopy. For this reason, air jet milling yields a pigment with higher reflection and different flop behavior relative to a pigment obtained by other known conditioning methods. Since no organic solvents are involved, the air jet milling process is a practical, environmentally friendly conditioning method. An expert utilizing the appropriate equipment and air pressure easily achieves the desired particle size. Additionally, depending on the set up, it is possible to run such a mill continuously. The requisite milling conditions are readily ascertained by measuring the pigment particle size, for example by an electron micrograph or by laser diffraction using a Fraunhofer diffraction instrument.

A preferred embodiment of this aspect of the present invention is the process wherein at least 95 percent of the particles in the conditioned pigment have a particle size in the range from 0.1 μm to 9 μm with at least 50 percent of the particles having a particle size in the range from 0.5 μm to 3.5 μm. Based on these average particle size ranges, it is clear that such pigments are used in the form of a pigment crude or a conditioned pigment. Preferably, at least 50 percent of the particles have a particle size in the range from 0.8 to 2.5 μm, especially wherein the conditioned pigment is a copper phthalocyanine pigment, most preferably a beta copper phthalocyanine. Preferably the conditioned copper phthalocyanine pigment is prepared by air jet milling a copper phthalocyanine crude, preferably an alpha or beta copper phthalocyanine crude.

The present invention alternatively relates to a colored seed having a coating that has been prepared by air jet milling from 1 to 40 parts by weight of inorganic filler in the presence of from 60 to 99 parts by weight of an organic pigment to yield a uniform blend of the inorganic filler and the organic pigment. In general, after the air jet milling step is completed the largest dimension of 95% of the particles in the resulting pigment composition is 18 μm or less, preferably 14 μm or less and most preferably about 7 to 10 μm, when measured for example by laser diffraction using a Fraunhofer diffraction instrument.

The inorganic filler is reduced in particle size in the presence of the organic pigment and uniformly blended with the organic pigment in the air jet mill. The organic pigment and inorganic filler are added to the air jet mill individually, for example as separate streams, or are blended prior to the air jet milling step. Typically, the organic pigment is blended with the inorganic filler prior to the air jet milling by wet or dry mixing of the components in the proper ratio. Wet mixing is carried out, for example, in the end step of a pigment preparatory process, or by blending the filler into an aqueous pigment slurry. Typically, a wet blended mixture needs to be dried and micro pulverized prior to the air jet milling step. Preferably, the organic pigment is dry blended with the inorganic filler in a suitable container or in blending equipment, such as the TURBULA mixer from W. Bachofen, Basel, Switzerland, or the P-K TWIN-SHELL INTENSIFIER BLENDER from Patterson-Kelley Division, East Stroudsburg, Pa. The organic pigment/inorganic filler blend is then subjected to the air jet milling procedure described above.

The pigment compositions are "uniform blends" of the filler and organic pigment, a uniform blend being a physical mixture of the filler and pigment wherein the filler particles are evenly distributed in the pigment and mostly uncoated by the pigment. The term "mostly" is intended to mean that although there may be some coated particles in the pigment composition, such coated filler particles do not constitute a large portion of the filler particles in the pigment composition. Similarly, the exterior surface of the seeds are coated with the pigment in substantial fashion. The term "physical mixture" means that the pigment and filler particles are distinct from each other, especially when the pigment composition is dispersed.

Generally, the present pigment compositions comprise from 60 to 99 parts by weight of the organic pigment and from 1 to 40 parts by weight of the filler. Preferably, the pigment compositions contain from about 65 to 95 parts by weight of the organic pigment and about 5 to 35 parts by weight of the filler, most preferably from about 70 to 90 parts by weight of the organic pigment and from about 10 to 30 parts by weight of the filler. The parts are relative to one another and, as to the two components, sums 100 parts by weight.

The expression "inorganic filler" means a substantially transparent inorganic pigment. For example, mica, kaolin, talc, wollastonite and natural or synthetic silica, e.g. glass, are well-known inorganic fillers that are suitable for use in the pigment compositions of the present invention. Talc, muscovite mica and kaolin are highly suitable inorganic fillers. Talc and transparent micas are especially suitable for use as an inorganic filler. Of the micas, muscovite, phlogopite, brolite and synthetic micas are the most suitable.

The inorganic filler is preferably used in its natural form, but includes treated transparent or semitransparent inorganic filler pigments, for example a mica treated with a metal oxide, or talc treated with an organic aliphatic compound, such as a long chain aliphatic acid. In general, the inorganic filler consists of primary filler particles having any geometric shape, but a flaked shape is preferred.

Especially suitable classes of organic pigments are the phthalocyanine. For example the blue alpha or beta copper phthalocyanine, most preferably a beta copper phthalocyanine or the halogenated copper phthalocyanine greens, like C.I. Pigment Green 7 or C.I. Pigment Green 36.

In general, the inorganic filler has a mean particle size in the range from 4 to 18 μm with 95% of the particles having a largest dimension of 70 μm or less prior to air jet milling. Preferably, 95% of the particles have a largest dimension below 60 μ, preferably below 50 μm, and a mean particle size in the range from 6 to 15 μm, preferably 8 to 12 μm, prior to air jet milling.

Generally, the organic pigment has an average particle size in the range of from 0.001 to 30 μm, preferably within the range from 0.005 to 3 μm, prior to the air jet milling step. Based on these average particle size ranges, it is clear that the organic pigment is used in the form of a pigment crude or a conditioned pigment. Additionally, the organic pigment can contain customary additives, such as texture improving agents, light stabilizers and/or anti flocculating agents.

The present invention is alternatively drawn to a colored seed having an exterior surface coated with at least one layer of a pigment concentrate that comprises from 1 to 40 parts by weight of an inorganic filler and from 60 to 99 parts by weight of an organic pigment relative to one another wherein said components have not been conditioned by air jet milling. The organic pigment has an average particle size of 0.001 to 10 μm. Preferably, the average particle size of the organic pigment is from 0.005 to 4 μm. Based on these average particle size ranges, it is clear that such pigments are used in the form of a pigment crude or a conditioned pigment. Preferably, the pigment is used in its aqueous presscake form as obtained, for example, by the isolation of the pigment after synthesis or conditioning. The inorganic filler preferably has an average particle size from 0.05 to 25 μm, more preferably from 0.1 to 10 μm.

In an alternative embodiment, the colored seed comprises a seed having an exterior surface coated with at least one layer of pigment concentrate that comprises from 85 to 99.5 parts by weight of an organic pigment, and from 0.5 to 15 parts by weight of a polar polymer or copolymer having a weight average molecular weight of not more than 300,000, relative to one another. Any polar polymer which provides the instant dispersing pigment behavior according to this invention and which preferably is approved by the Environmental Protection Agency can be used. Preferably, the polar polymer or copolymer is a polyvinyl pyrrolidone or copolymer thereof with an average molecular weight of above 5000.

The organic pigment for each of the embodiments can be selected from the group consisting of azo, azomethine, methine, anthraquinone, phthalocyanine, perinone, perylene, diketopyrrolopyrrole, thioindigo, iminoisoindoline, iminoisoindolinone, quinacridone, flavanthrone, dioxazine, indanthrone, anthrapyrimidine and quinophthalone pigments and mixtures thereof.

Surprisingly, it was discovered that the organic pigments prepared and treated according to the present invention and coated on seeds can enhance germination synergistically when the pigment or pigment concentrates additionally contain growth promoters such as certain metal complexes containing transition elements like for example manganese, iron, copper, molybdenum or Zn. Appropriate metal complexes are for example the $C_1$–$C_4$alkylene (preferably ethylene) diamine tetraacetate complexes. An especially suitable growth promoter is Zn disodium ethylene diamine tetraacetate, which is commercially available from Ciba Specialty Chemicals under Librel Zn.

Such growth promoters are preferably added before, during or after the pigment preparation process for example before or after air-jet milling or during the wet blending process when treated with a polar polymer such as polyvinyl pyrrolidone.

Preferably the pigment or pigment concentrate according to this invention contains 50 to 95 percent by weight of the pigment or pigment concentrate and 5 to 50 parts by weight of the growth promoting additive, preferably 60 to 80 parts by weight of the pigment or pigment concentrate and 20 to 40 parts by weight of the growth promoting additive.

In a preferred method the growth promoter additive is blended with the pigment or pigment concentrate in an economic and environmentally friendly dry blending process in equipment known in the industry.

Furthermore, it is possible to apply the growth promoting additive together with the pigment or pigment concentrate in the above given inventive pigment to growth promoter ratio directly during the seed coating process executed as known in the agro chemical industry.

The seeds described herein are used to grow plants, fruits or vegetables. The particular type of seed is not important. In general, the seeds will have a somewhat spherical shape, perhaps with flat edges or sides. The colorant and growth-promoting additive described herein will be applied to the exterior surface of the seeds.

In this application, the expression "dry pigment form or dry pigment concentrates" is intended to mean a composition, which is used to pigment seeds. Thus, the present dry pigment form or pigment concentrates do not include the pigmented seeds. Accordingly, the inventive pigment form or pigment concentrates can consist essentially of the organic pigment and optionally filler, and are generally powders. However, the inventive pigment form or pigment concentrates can also contain specific organic additives for pigment compositions, for example the known texture improving agents. The inventive pigment forms or pigment concentrates are capable of forming a substantially uniform and stable aqueous dispersion.

Appropriate other organic additives are for example the known texture-improving agents including fatty acids having at least 12 carbon atoms, and amides, esters or salts of fatty acids. Typical fatty acid derived texture-improving agents include fatty acids such as stearic acid or behenic acid, and fatty amines such as laurylamine, or stearylamine. In addition, fatty alcohols or ethoxylated fatty alcohols, polyols such as aliphatic 1,2-diols or polyvinylalcohol, and polyvinyl pyrrolidone, polyacrylic acid and copolymers thereof, epoxidized soy bean oil, waxes like carnauba wax. Rosin, rosin acids or rosin acid salts, hydrogenated rosin and rosin derivatives, resin acids such as hydrogenated abietic acid or resin acid salts are particularly suitable organic additives.

Hydrogenated abietic acid, rosin, hydrogenated rosin, rosin derivatives and rosin acid salts are preferred texture-improving additives. The rosin acid and resin acid salts are preferably calcium, magnesium, strontium and aluminum salt.

The organic additive in the dry pigment concentrate is added at the end of the pigment synthesis step or to the pigment press cake or it is incorporated to the organic pigment/talc blend when it is dry or wet blended. Preferably, these additives are added before the isolation or drying of the organic pigment after synthesis or conditioning.

The amount of the texture-improving additive is 0.05 to 30 parts by weight, preferably 1 to 20 parts in 100 parts by weight of the dry pigment concentrate according to this invention.

In an additional aspect of the present invention, the pigment concentrate contains a polar organic additive such as the above mentioned polyvinyl alcohol, polyacrylic acid or particularly polyvinyl pyrrolidone. Applicants discovered that the addition of the polar polyvinyl pyrrolidone further enhances the wetability of the pigment.

Therefore, such pigment concentrates are instantly dispersed when added to an aqueous liquid media and do not need a special dispersion step utilizing an expensive equipment like high speed mixers or dispersion mills.

Preferably, a polyvinyl pyrrolidone approved by the Environmental Protection Agency such as polyvinyl pyrrolidone with a molecular weight of above 5000 is incorporated into an aqueous pigment/inorganic filler slurry which is then spray dried to generate low dusting, easily flowable and easily wetable pigment concentrates. Particularly preferred pigment concentrates containing the polar organic additive can be prepared in accordance with the teachings in U.S. Pat. No. 6,063,182, which is incorporated herein by reference.

As described more fully therein, the particularly preferred pigment concentrates are obtained by spraying an aqueous dispersion. A highly concentrated pigment presscake is slurried in any suitable device at temperatures between 5 to 90° C., preferably 20 to 60° C., such as, for example, a Cowles™ disperser, in the presence of the aqueous additive solution as illustrated in the examples below to obtain a homogeneous aqueous dispersion. A person skilled in the art can then easily determine suitable conditions for spray drying the homogeneous aqueous dispersions.

Low viscosity aqueous pigment dispersions with a solids content of above 15% or, depending on the pigment and polymeric additive or additive mixture, solids contents of 20% and above can be easily generated. Despite the high pigment concentration, these pigment dispersions have the advantage that they are liquid, easily flowable and ideally suited for spray drying. Spray drying is a well-known drying technology in the chemical industry. Any equipment, which is conventional for spray drying for example a disc or nozzle spray dryer can be used to spray, dries the inventive pigment compositions. Suitable commercially available equipment includes the BOWEN BLS spray dryer from Bowen or the NIRO ATOMIZER from NIRO Company. Due to their high solids content, the pigment dispersions are dried rapidly and economically by spray drying, yielding unique pigment compositions composed of micro granules. The additives according to this invention are homogeneously distributed in the stir-in pigment compositions and also serve as the binder for the micro granules.

Typically, the micro granules have a size in the range of from 1 to 3000 μm, preferably from 3 to 1000 μm when suspended in a water-immiscible solvent such as xylene and observed under the light microscope. They can have any shape. The shape and size of the micro granules are influenced by several parameters such as the kind and particle size of the pigment, the kind and concentration of the additive or additive mixture respectively, as well as the spray drying conditions and the spray dryer equipment. The micro granules are generally less dusty and can be more easily handled than conventionally dried and micro pulverized pigments.

The amount of the polar organic additive is 0.05 to 15 parts by weight, preferably 1 to 10 parts in 100 parts by weight of the dry pigment concentrate according to this invention.

Remarkably, the dry instant pigment forms and pigment concentrates according to the present invention show an outstanding dispersibility and compatibility behavior to the seed media. Thus, the seeds are easily colored and marked by the inventive pigment forms and pigment concentrates providing a consistent colored material with a long shelf life. The colorant layer is provided on the seed over substantially their entire surface resulting in homogeneously colored seed.

Growth promotion is a most valuable effect because it enhances the yield of the produce. Thus, the faster the germination the less prone are seed losses due to birds or bad weather conditions like strong rain, wind or dryness. Growth promotion for grass for example is particularly useful on fields and slopes to cut the erosion, on sport fields or lawns for safety and aesthetic reasons respectively. A particularly strong growth effect was observed on grass seeds colored with a pigment form or pigment concentrate using a beta copper phthalocyanine that had been conditioned using air jet milling, which is described above and is subject of a co-pending application. Evidence of improved germination effects from the selected colorant is provided in the examples.

Any number of techniques and equipment known to those skilled in the art of seed coating may be applied for the seed coloring by the dry pigment forms or pigment concentrates. The process may be continuous or batch, and typically involves tumbling of the seeds in the presence of the present dry pigment forms or pigment concentrates.

An alternative application process involves a liquid media in which the pigment forms or pigment concentrates have been dispersed. Examples of suitable liquid media include an aqueous, organic or aqueous/organic media, which may additionally contain biologically active components, binders or other coating ingredients. Preferably, the liquid media is primarily an aqueous medium with optionally only minor amounts of organic materials. Most preferably, the mixture of concentrate and liquid media produces a dispersion having an aqueous continuous phase with pigment concentrate suspended therein, which is optionally coated with a surfactant or dispersant. The dispersion should be substantially free of organic, water-immiscible solvents, which would produce an emulsion. The concentration of the pigment concentrate (on a dry basis) is about 0.1 to 10 percent of the overall composition, more preferably 0.1 to 3, most preferably, 0.1 to 1 percent. Preferably the pigment concentrates are treated with a polar organic additive as described above when practicing this embodiment of the invention. The inventive instant pigment concentrates are quickly wetted and due to its high pigment concentration extremely economic. The reduced level of liquid media lowers the generation of wastewater and reduces the energy requirements for producing a "dry" seed.

In yet another method, the dry pigment form or pigment concentrate or a liquid media as described above is applied onto a seed that has been coated with an aqueous and/or organic liquid film-forming substance that can optionally contain an active ingredient, defoamers, and a binder. Examples of active ingredients are fungicides, insecticides, rodenticides, herbicides, bird repellants, nematocides, miticides, growth regulants, and nutrients. Alternatively, the seed is coated with said film-forming substance and then subsequently provided with a coloring layer using the dry instant pigment concentrate or pigment concentrate-containing liquid media described herein. An alternative means for applying the colorant includes the steps of applying uncolored seeds over a surface and subsequently spraying an aqueous-based solution containing the selected pigment onto the surface-laid seeds.

Furthermore, the liquid media containing the above mentioned active ingredients, defoamers or binders can be directly colored by the addition of an active coloring amount of the dry pigment form or pigment concentrate and then be applied to the seeds.

The use of dry instant pigment form or pigment concentrate provide characteristic coloristic pigment properties to seeds such as a high opacity and a homogenous intense color in an effective, economical and environmentally friendly manner by eliminating or reducing liquid waste product. The resulting colored seeds also offer the advantage that the colorant layer is substantially non-soluble in water and therefore will not be eliminated due to exposure to rain or humid conditions. The colored seeds also exhibit improved color fastness when exposed to light relative to seeds that have been colored with dyes. Additionally, the resulting dry pigment layer can advantageously promote growth.

The following examples further describe some embodiments of the invention, but do not limit the scope of the invention. In the examples, all parts are by weight unless otherwise indicated.

EXAMPLES

Example 1

300 grams IRGALITE Red C2B from Ciba Specialty Chemicals Corp. which is a rosin and resin acid salt treated C.I. Pigment Red 48.2 is blended on a roller gear with 50 grams Canfil 7 from Canada Talc Ltd., which has an average particle size of 7 μm and 100 grams Librel Zn from Ciba Specialty Chemicals.

The resulting blend is micro pulverized in an assemble micro pulverizer (The BANTAM, type G 90 from the American Marietta Company) using a 0.027 inch round hole screen and a rotating speed of 14500 RPM yielding an easily dispersible dry pigment concentrate which homogeneously colors seeds in a strong red color and additionally promotes growth.

Example 2

The procedure of Example 1 is repeated using instead of Canfil 7, Ultra talc 609 from Barrets Mineral Inc. which has an average particle size of 0.8 μm as an inorganic filler yielding a dry pigment concentrate which is ideally suited for homogeneously coloring seeds in a consistent red color and which additionally promote growth.

Example 3

The procedure of Example 2 is repeated using instead of IRGALITE Red C2B IRGALITE Blue LGE from Ciba Specialty Chemicals Corp. which is a hydrogenated rosin treated C.I. Pigment Blue 15.3 yielding a dry pigment concentrate which is ideally suited for homogeneously coloring seeds in a consistent blue color and which additionally promote growth.

Example 4

1000 grams IRGALITE Blue GE granules from Ciba Specialty Chemicals Corp., which is a hydrogenated rosin treated C.I. Pigment Blue 15.3 is pulverized in an assemble micro pulverizer (The BANTAM, type G 90 from the American Marietta Company) using a 0.125 inch round hole screen and a rotating speed of 7000 RPM.

900 grams of the above resulting pulverized pigment is blended with 225 grams Canfil 7 and 300 grams Librel Zn from Ciba Specialty Chemicals. The mixture is air jet milled with a Micro-Jet® air jet mill (from Fluid Energy Aljet, Plumsteadville Pa.) to a top particle size of below 10 $\mu$m. The resulting blue dry pigment concentrate is ideally suited for homogeneously coloring seeds in a consistent blue color. Grass seeds colored with such a blue pigment concentrate show the advantage of a notably faster growth behavior versus the uncolored or differently treated seeds.

Example 5

Example 3 is repeated using instead of C.I. Pigment Blue 15.3 hydrogenated rosin treated C.I. Pigment Green 7 yielding a dry pigment concentrate, which is ideally suited for homogeneously coloring seeds in a consistent green color Example 6

A 4 liter WARING Blender from Cole-Parmer Instrument Company is charged with 2286 grams aqueous presscake containing 802 grams dry weight isoindolinone pigment IRGAZIN YELLOW 3 RLTN (C.I. Pigment Yellow 110 from Ciba Specialty Chemicals Corp., Newport Del.).

In a one-liter glass beaker 59.6 grams of an aqueous polyvinylpyrrolidone solution (LUVISKOL K30 from BASF Corp.) are dissolved in 200 ml water. Then 80.2 grams ULTRA Talc 609 from Barretts Minerals Inc. are added into the aqueous resin solution and stirred until completely wetted.

The aqueous talc/resin mixture is added to the yellow isoindolinone pigment presscake in the WARING blender. The mixture is blended at medium to high speed generating easily flowable liquid yellow pigment dispersion.

Two batches of the above aqueous yellow pigment dispersion are combined, followed by spray drying in a pilot plant spray dryer (the BOWEN BLS from Bowen) yielding 1.78 kg yellow pigment concentrate in a micro granule form. 100 grams of the above pigment concentrate is blended with 100 grams Librel Zn in a Turbula mixer from W. Bachofen, Basel. The blend, which can instantly be incorporated into an aqueous liquid media, employed to coloring seeds homogeneously in a yellow color. Preparation of liquid media is described more fully in example 8.

Example 7

The above procedure is repeated using instead of IRGAZIN Yellow 3RLTN 3050 grams of a press cake containing 1059 grams of the C.I. Pigment Red 48.2, IRGALITE Red 2BP from Ciba Specialty Chemicals Corp., 88.2 grams LUVISKOL K-30 and 130 grams Ultratalc 609 yielding a red pigment concentrate in a micro granule form which can instantly be incorporated into an aqueous liquid media employed to coloring seeds homogeneously in a red color.

Example 8

One-gallon porcelain testing jug is charged with one quart distilled water. Using a laboratory stirrer, 20 oz equal blends XL (R-[(2,6-dimethylphenyl)-methoxyacetylamino]-propionic acid methyl ester) an TL (N-(2,6-dimethylphenyl)-N-(methyloxyacetyl)alanine methyl ester) aprons and one teaspoon (about 1.5 grams) of the blue pigment concentrate prepared according to Example 4 are added and stirred until a homogeneous pigment dispersion is generated. In roller tumblers containing 2 pounds each of various seeds, the above blue dispersion is added to each and rolled for 30 minutes. The mixture is removed and the liquid is decanted. The solids are placed on a drying tray and dried with forced air for 72 hours, resulting in commercially acceptable intense blue stained seeds.

Surprisingly, under controlled testing conditions: canola, cotton, corn, soy bean, Kentucky Blue and Kentucky fescue grass seeds all exhibited faster germination when colored with the above blue dispersion within 60 hours, whereas the uncolored seeds indicated little growth.

Example 9

500 grams of Copper Phthalocyanine Blue Crude (a beta copper phthalocyanine from SUN Chemical) having a needle-prismatic particle shape and an average particle size of from 2.0–3.0 $\mu$m, but containing particles of up to 44 $\mu$m, is air jet milled such that the larger particles are reduced to a particle size of below 9 $\mu$m on a MICRO-JET® air pulverizer from Fluid Energy Aljet, Plumsteadville Pa. The resulting product shows a particle size distribution of 30% from 0.2 to 0.8 $\mu$m, 40% from 0.8 to 2.1 $\mu$m and 30% from 2.1 to 8 $\mu$m measured by a laser diffraction particle analyzer (MICROTRAC).

The electron micrograph shows particles with a marked prismatic shape wherein 50 percent of the particles display a length of from 2 to 4.5 $\mu$m lengths and a width of from 0.3 to 1.1 $\mu$m. The crystals show clear broken edges with few small splinter particles below 0.2 $\mu$m.

100 grams of the above copper phthalocyanine pigment is blended with 100 grams Librel Zn in a Turbula mixer from W. Bachofen, Basel. The dry copper phthalocyanine pigment blend is ideally suited for homogeneously coloring seeds in a consistent blue color. Surprisingly, faster corn, canola, cotton, soy bean, Kentucky blue and Kentucky fescue grass seeds germination was observed when they were colored with the blue dispersion above within 48 hours, whereas the uncolored seeds indicated little growth.

What is claimed is:

1. A colored seed having an exterior surface coated with at least one layer comprising an instant pigment form or pigment concentrate and a metal complex growth-promoting additive, wherein at least 95 percent of the pigment particles in the corresponding pigment form or pigment concentrate have a particle size in the range from 0.1 to 9 $\mu$m with at least 50 percent of the pigment particles having a particle size in the range from 0.5 to 3.5 $\mu$m.

2. A colored seed having an exterior surface coated with at least one layer comprising an instant pigment concentrate and a metal complex growth-promoting additive, wherein the pigment concentrate comprises from 1 to 40 parts by weight of an inorganic filler and from 60 to 99 parts by weight of an organic pigment having an average particle size of 0.001 to 10 $\mu$m, where the parts by weight are relative to one another and sum 100 parts.

3. A colored seed according to claim 1, wherein the pigment particles have been conditioned by air jet milling.

4. A colored seed according to claim 2, wherein the organic pigment and inorganic filler are conditioned by air jet milling.

5. A colored seed according to claim 2, wherein the average particle size of the organic pigment is from 0.005 to 4 $\mu$m.

6. A colored seed of claim 2, wherein the average particle size of the inorganic filler is from 0.05 to 25 μm.

7. A colored seed of claim 6, wherein the average particle size of the inorganic filler is from 0.1 to 10 μm.

8. A colored seed having at least one layer comprising an instant pigment concentrate that comprises from 85 to 99.5 parts by weight of an organic pigment, and from 0.5 to 15 parts by weight of a polar polymer or copolymer having a weight average molecular weight of not more than 300,000.

9. A colored seed according to claim 8, wherein said polar polymer or copolymer is a polyvinyl pyrrolidone or copolymer thereof with an average molecular weight of above 5000.

10. A colored seed of claim 1, wherein the organic pigment is selected from the group consisting of azo, azomethine, methine, anthraquinone, phthalocyanine, perinone, perylene, diketopyrrolopyrrole, thioindigo, iminoisoindoline, iminoisoindolinone, quinacridone, flavanthrone, dioxazine, indanthrone, anthrapyrimidine and quinophthalone pigments and mixtures thereof.

11. A colored seed of claim 1, wherein the organic pigment is selected from the group consisting of azo, phthalocyanine and dioxazine pigments and mixtures thereof.

12. A colored seed of claim 1, wherein the organic pigment is a copper phthalocyanine or a halogenated copper phthalocyanine.

13. A colored seed of claim 1, wherein the pigment of the organic pigment form is an air-jet milled copper phthalocyanine.

14. A colored seed of claim 2, wherein the organic pigment is a copper phthalocyanine or a halogenated copper phthalocyanine and the inorganic filler is selected from the group consisting of mica, kaolin, talc, wollastonite, natural silica, synthetic silica and mixtures thereof.

15. A colored seed of claim 14, wherein the inorganic filler is talc.

16. A colored seed according to claim 1, wherein the metal of said metal complex is selected from the group consisting of manganese, iron, copper, molybdenum, zinc and mixtures thereof.

17. A colored seed according to claim 1, wherein said growth promoting additive is zinc disodium ethylenediamine tetraacetate.

18. A colored seed according to claim 1, wherein the ratio of said pigment or pigment concentrate to growth promoting additive is 50 to 95 parts by weight of the pigment or pigment concentrate to 5 to 50 parts by weight of the growth promoting additive.

19. A colored seed according to claim 1, wherein the ratio of said pigment or pigment concentrate to growth promoting additive is 60 to 80 parts by weight of the pigment or pigment concentrate to 20 to 40 parts by weight of the growth promoting additive.

20. A colored seed of claim 1, wherein said pigment concentrate further comprises a texture improving agent selected from the group consisting of a fatty acid, a fatty amine, a fatty alcohol or ethoxylated fatty alcohol, an aliphatic 1,2-diol or polyvinylalcohol, a polyvinyl pyrrolidone, polyacrylic acid or polyacrylic acid copolymers, an epoxidized soy bean oil, a wax, a rosin, a rosin derivative, a resin, a resin acid and a resin acid salt.

21. A colored seed according to claim 20, wherein said texture improving agent is a polyvinyl pyrrolidone or copolymer thereof with an average molecular weight of above 5000.

22. A process for coloring seeds which comprises contacting a plurality of seeds with a dry pigment form or pigment concentrate and a metal complex growth-promoting additive or with a liquid media containing said pigment form or pigment concentrate and said growth promoting additive wherein at least 95 percent of the pigment particles in the corresponding pigment form or pigment concentrate have a particle size in the range from 0.1 to 9 μm with at least 50 percent of the pigment particles having a particle size in the range from 0.5 to 3.5 μm.

23. A process for coloring seeds which comprises contacting a plurality of seeds with a dry pigment concentrate and a metal complex growth promoting additive or with a liquid media containing said pigment concentrate and said growth promoting additive where the pigment concentrate comprises from 1 to 40 parts by weight of an inorganic filler and from 60 to 99 parts by weight of an organic pigment having an average particle size of 0.001 to 10 μm, where the parts by weight are relative to one another and sum 100 parts to form a coating thereon.

24. A process for coloring seeds which comprises contacting a plurality of seeds with a dry pigment concentrate and a metal complex growth promoting additive or with a liquid media containing said pigment concentrate and said growth promoting additive wherein the pigment concentrate comprises from 0.5 to 15 parts by weight of a polar polymer or copolymer having a weight average molecular weight of not more than 300,000 and from 85 to 99.5 parts by weight of an organic pigment to form a coating thereon.

25. A process according to claim 22, wherein a plurality of unpigmented seeds are contacted with the dry pigment form or pigment concentrate and said growth promoting additive or liquid media containing said pigment form or pigment concentrate and said growth promoting additive by spraying after said unpigmented seeds are applied to a surface.

26. A process according to claim 23 wherein a plurality of unpigmented seeds are contacted with the dry pigment concentrate and said growth promoting additive or liquid media containing said pigment concentrate and said growth promoting additive by spraying after said unpigmented seeds are applied to a surface.

27. A process according to claim 24, wherein a plurality of unpigmented seeds are contacted with the dry pigment concentrate and said growth promoting additive or liquid media containing said pigment concentrate and said growth promoting additive by spraying after said unpigmented seeds are applied to a surface.

* * * * *